US006337049B1

(12) United States Patent
Tamari

(10) Patent No.: US 6,337,049 B1
(45) Date of Patent: Jan. 8, 2002

(54) SOFT SHELL VENOUS RESERVOIR

(76) Inventor: Yehuda Tamari, 21 Singworth St., Oyster Bay, NY (US) 11771-3703

(*) Notice: Subject to any disclaimer, the term of this patent is extended or adjusted under 35 U.S.C. 154(b) by 0 days.

(21) Appl. No.: 09/141,960

(22) Filed: Aug. 28, 1998

(51) Int. Cl.[7] .............................. A61M 1/14; A61M 1/34; A61M 37/00; A61M 1/00; A61B 19/00
(52) U.S. Cl. .......................... 422/44; 422/45; 604/4.01; 604/6.15; 604/408; 604/327
(58) Field of Search ................. 604/4.01, 6.15, 604/317, 327, 403–411, 5.01, 319–21, 322; 128/DIG. 3, 24

(56) References Cited

U.S. PATENT DOCUMENTS

| 3,849,071 A | | 11/1974 | Kayser |
| 3,907,504 A | | 9/1975 | Hammond |
| 4,466,888 A | * | 8/1984 | Verkaart |
| 4,622,032 A | | 11/1986 | Katsura |
| 4,795,457 A | | 1/1989 | Cooney |
| 4,976,708 A | * | 12/1990 | Oshiyama ................... 604/408 |
| 5,049,146 A | | 9/1991 | Bringham |
| 5,078,677 A | * | 1/1992 | Gentelia et al. |
| 5,352,218 A | | 10/1994 | Buckley |
| 5,382,227 A | | 1/1995 | Riquier |
| 5,563,584 A | | 10/1996 | Rader et al. |
| 5,573,526 A | * | 11/1996 | Hess ........................... 604/408 |
| 5,580,349 A | | 12/1996 | Thor |
| 5,738,645 A | | 4/1998 | Plotkin |
| 5,858,015 A | * | 1/1999 | Fini ............................ 604/403 |
| 6,017,493 A | * | 1/2000 | Cambron et al. ............. 422/44 |

OTHER PUBLICATIONS

Wallock M, et.al.: Single pump mechanically aspirated venous drainage (SPMAVD) for cardiac reoperation Perfusion 1996;11(4):351–353.
McKusker K et al. High–flow femoro–femoral bypass utilizing small cannulae and a centrifugal pump on the ve Perfusion 1992;7:295–300.
Schonberger J. Systemic blood activation with open and closed venous reservoirs. Ann Thorac Surg 1995;59:1549–55.

Enclosed copy of prior reservoir; Got from Ken Broeker @ Harmac Med Products Buffalo NY.

Pall Autovent–3SV Blood Filter. Pall Biomedical Products Corporation, East Hills, NY. From brochure E–AV3S/DATA–P29315M, copyright 1993.

* cited by examiner

Primary Examiner—Angela D. Sykes
Assistant Examiner—Patricia M Bianco

(57) ABSTRACT

The venous reservoir accommodates variations in the total volume of blood circulating in the extracorporeal circuit during cardiopulmonary bypass (CPB). It is connected between the patient and the arterial pump and serves as a compliance chamber. Venous drainage by gravity alone provides an inadequate rate of blood return during procedures such as minimally invasive cardiac surgery and bypass via femoral cannulation. In these cases the resistance of the venous cannula limits the maximum achievable flow. Vacuum augmented venous drainage (VAVD) is a technique that overcomes flow limitations by applying suction to the hard shell reservoir thereby increasing the pressure difference between the venous site and venous reservoir. VAVD allows for a decrease in the inner diameter of the venous line, thereby reducing prime volume, as well as the use of a smaller cannula that translates to an easier insertion, a better surgical view, and a smaller surgical incision. VAVD precludes the use of the safer, soft-shell closed venous reservoir (bag) unless a more expensive and complicated two-pump system is used. The present invention describes a soft-shell venous reservoir that allows VAVD using a single pump. The invention describes a soft shell reservoir that is sealed within a, preferably, clear rigid housing. A gas port connected to the space between the bag and rigid housing is used to adjust the pressure within that space: it allows the user to adjust the "atmospheric" pressure about the external walls of the soft-shell reservoir. Another aspect of the invention improves gas bubble removal.

7 Claims, 10 Drawing Sheets

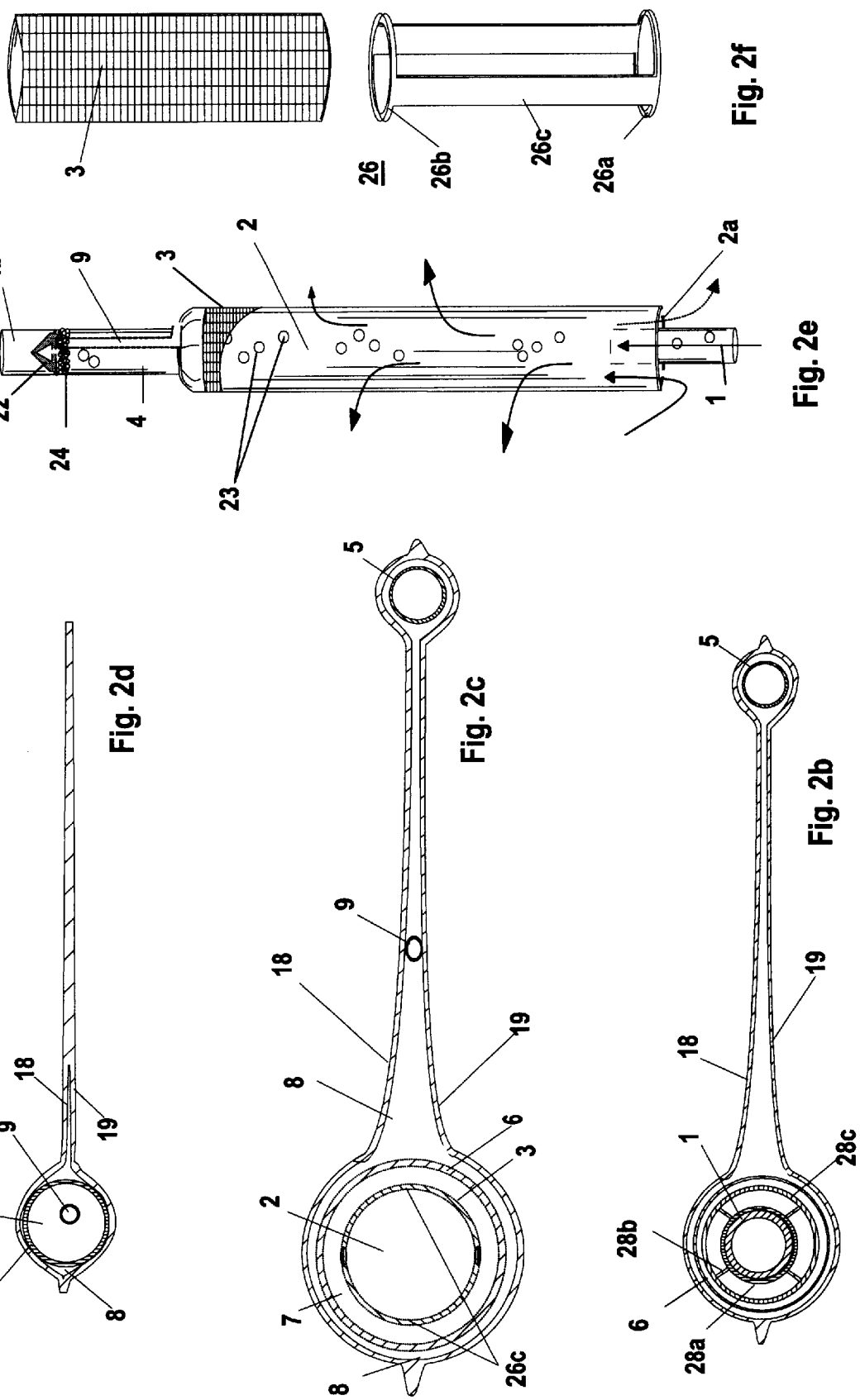

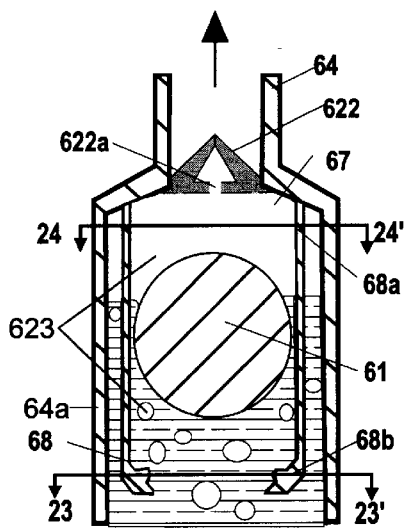
Fig. 6a
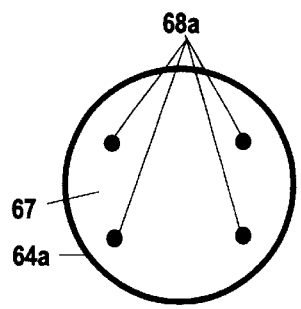
Fig. 6b
Fig. 6c
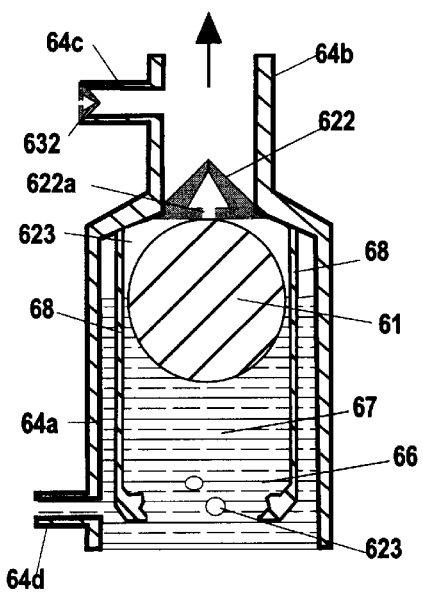
Fig. 6d

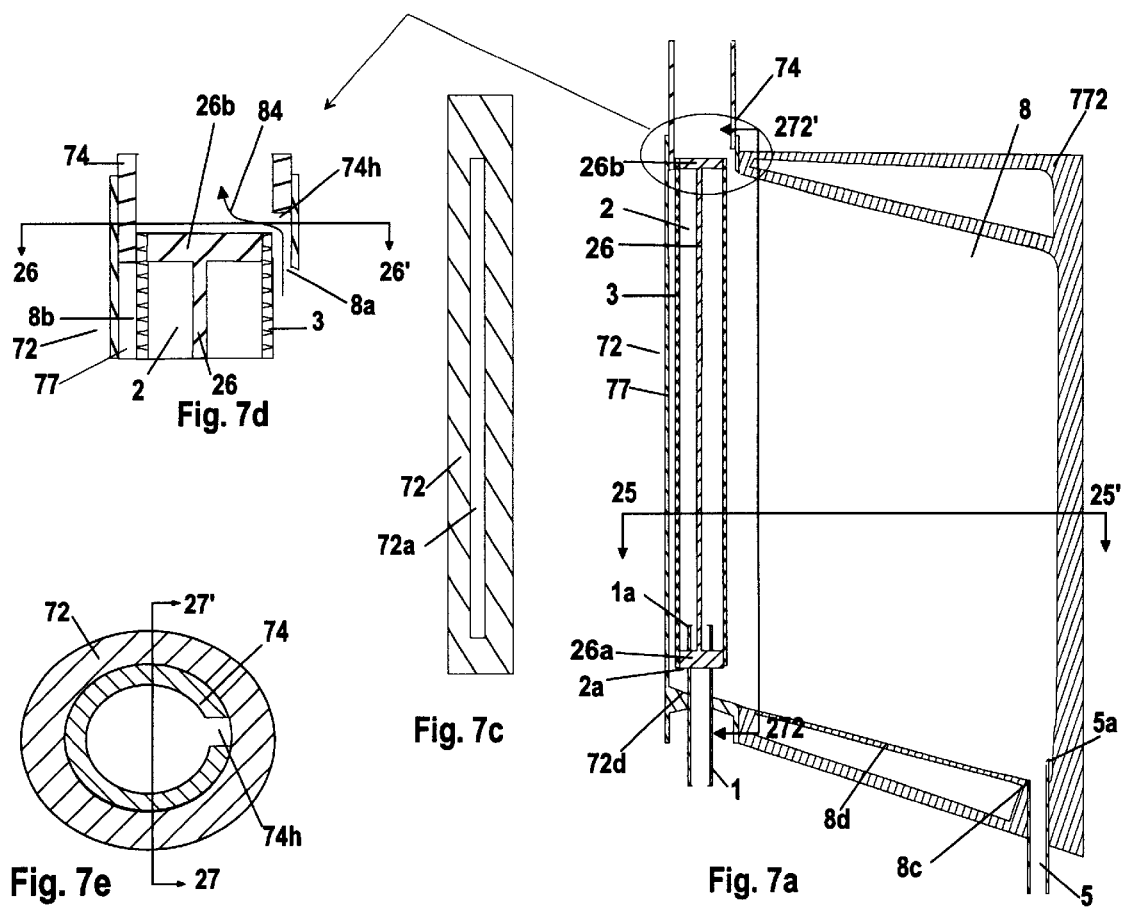
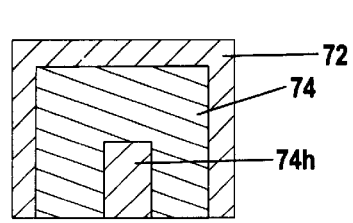
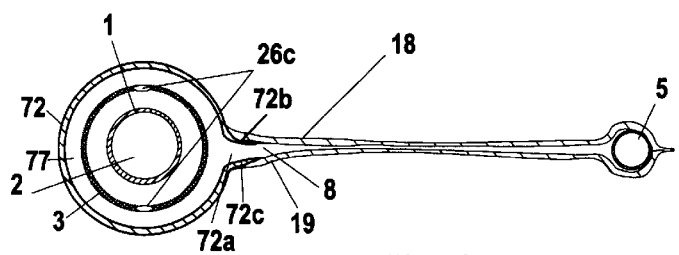

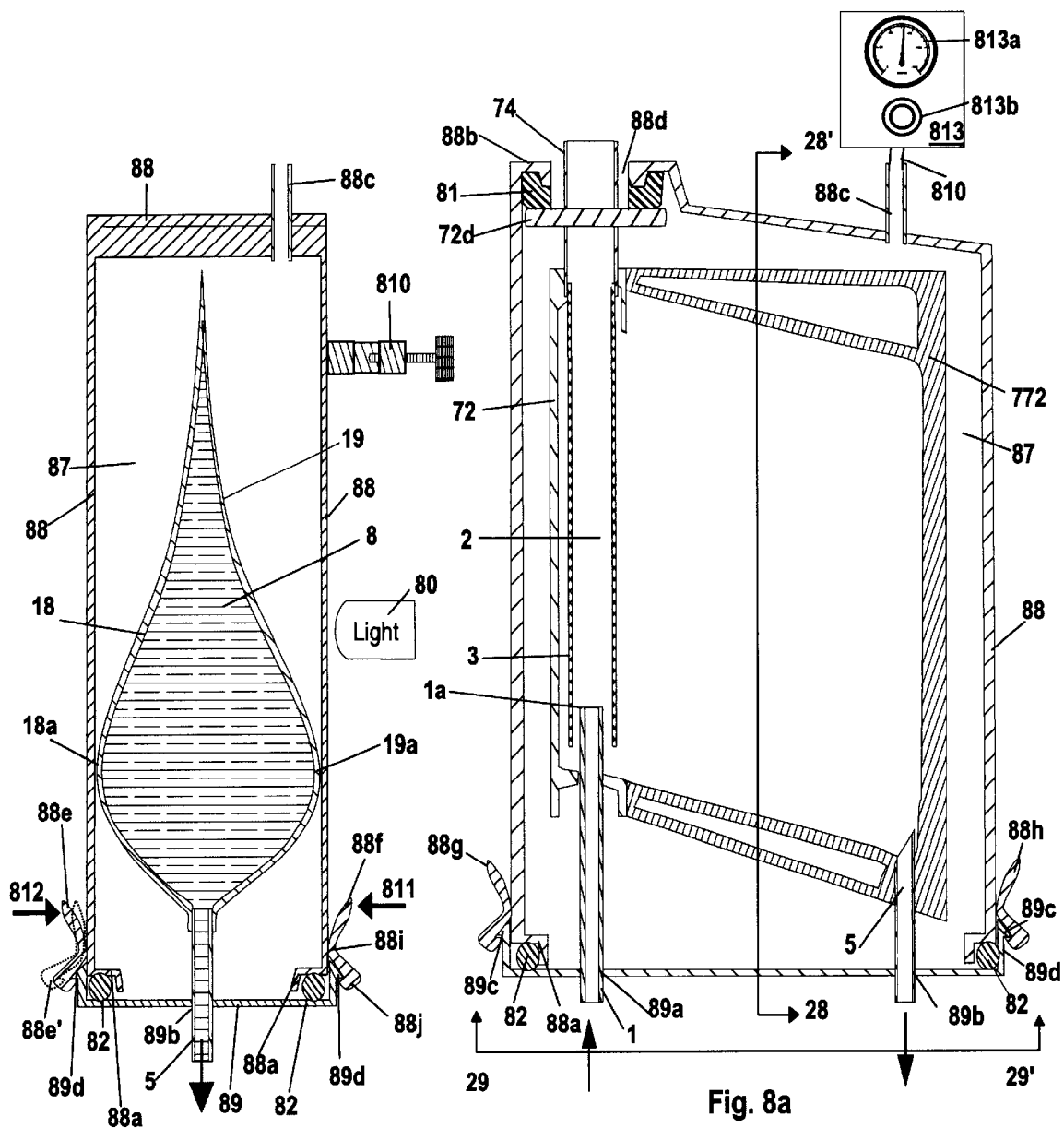
Fig. 8b
Fig. 8a
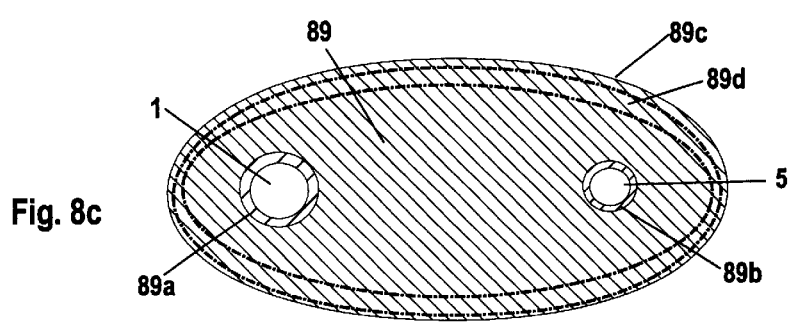
Fig. 8c

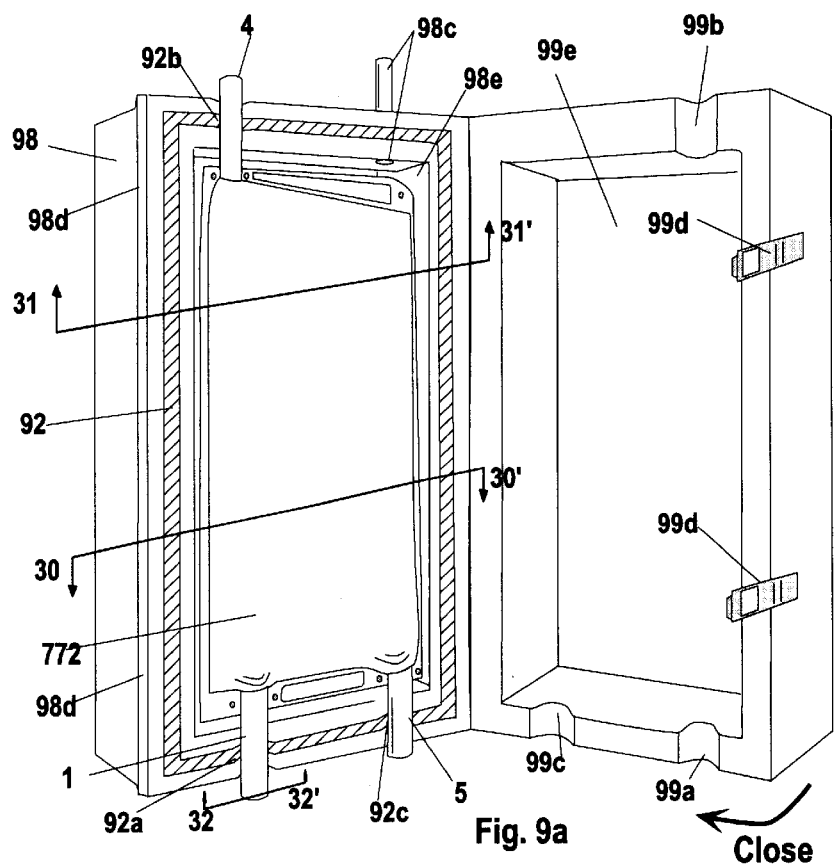
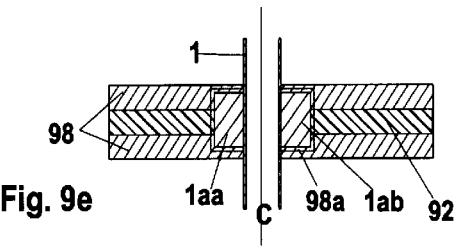
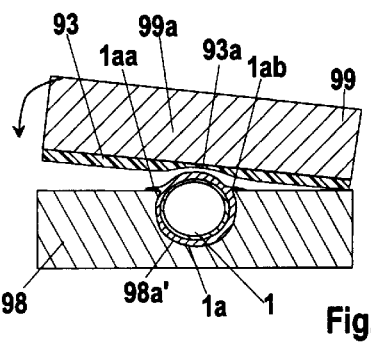
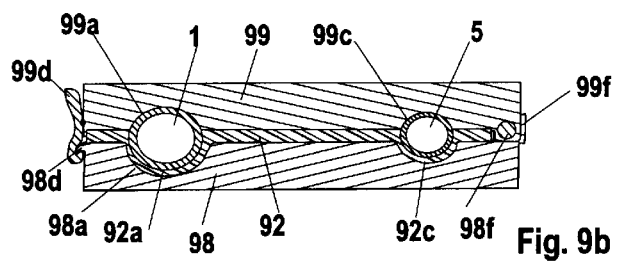
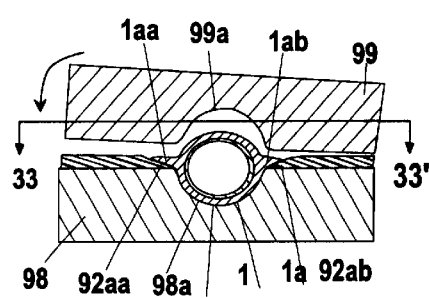
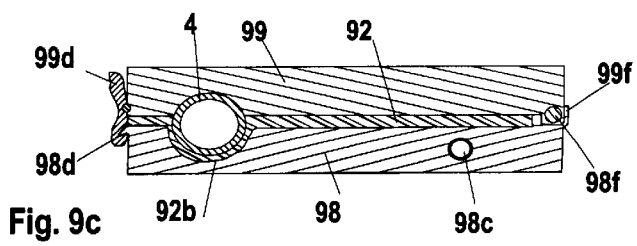

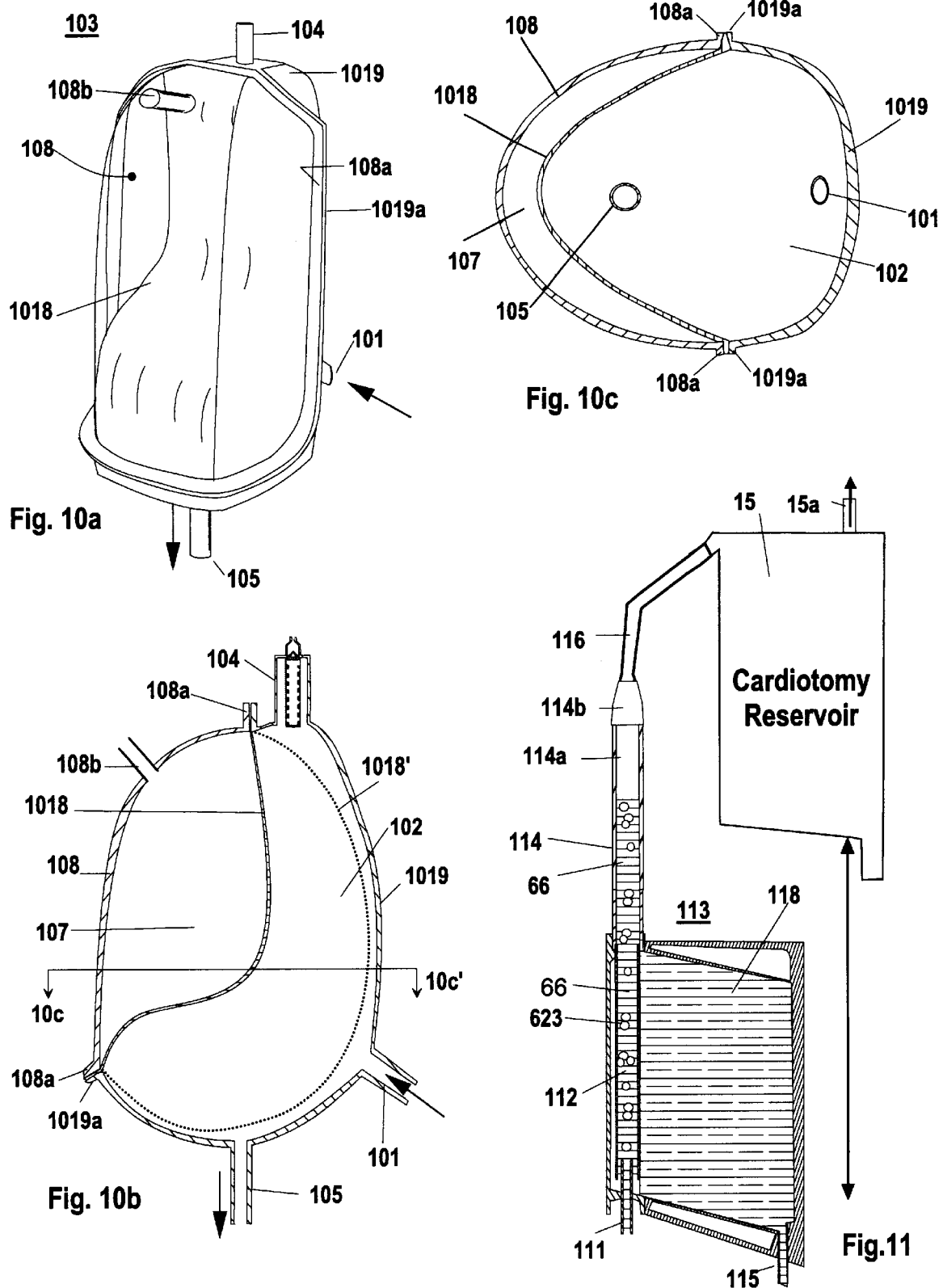

SOFT SHELL VENOUS RESERVOIR

GOVERNMENT INTERESTS

This invention was in part made with government support under an SBIR Grant #R44HL-55034 awarded by the National Institute Health, National Heart, Lung, and Blood Institute. As such the government may have certain rights in the invention.

BACKGROUND OF THE INVENTION

1. Field of the Invention

The invention is a blood reservoir with at least one pliable wall. It innovates the art in at least two ways. First, the compliant reservoir is sealed within a rigid housing allowing control of the "atmospheric" pressure surrounding the bag, and therefore the pressure at which the bag would collapse. This first invention enables vacuum augmented venous drainage (VAVD) with a collapsible soft-shell reservoir (i.e. venous bag) and is particularly useful for cardiopulmonary bypass. Second, the invention has a tubular structure with a screened wall that improves gas bubble removal from blood transiting the collapsible reservoir.

2. Description of the Prior Art

Blood is routinely pumped outside the body during dialysis, cardiopulmonary bypass, and long term cardiac and/or respiratory support (e.g. extracorporeal membrane oxygenation, ECMO). In general, blood flows from the venous side of the patient to a venous reservoir that is usually maintained at atmospheric pressure. Blood flow from the patient to the reservoir is a function of the resistance of the fluid conduit between patient and reservoir, and the pressure difference between patient and reservoir. When the reservoir is maintained at atmospheric pressure, that pressure difference is the height difference between patient and reservoir; the resulting flow is referred to as gravity drainage. Venous drainage by gravity alone provides inadequate return during procedures such as minimally invasive cardiac surgery and bypass via femoral cannulation. Usually it is the resistance of the venous cannula that limits the flow achievable. Vacuum augmented venous drainage (VAVD) is a technique that overcomes flow limitations by applying suction to the hard shell reservoir thereby increasing the pressure difference between the venous cannulation site and venous reservoir. VAVD allows for a decrease in the inner diameter of the venous line, thereby reducing prime volume, and enabling the use of a smaller cannula, which translates to an easier insertion, a better surgical view and a smaller surgical incision. This method precludes the use of the safer soft-shell closed venous reservoir (venous bag) unless a more expensive and complicated two-pump system is used (see McKusker K, Hoffman D, Maldarelli W, Toplitz S, and Sisto D. High-flow femoro-femoral bypass utilizing small cannulae and a centrifugal pump on the venous side. Perfusion 1992; 7:295–300).

Clinically, a venous bag is used because it provides significant safety features. If the bag empties, it collapses, thereby preventing gross air from being pumped to the patient. It usually has no air-blood interface, and it requires no antifoam agents that can embolize into the blood. A recent study by Schonberger et al (Schonberger JPAM, Everts PAM, and Hoffmann JJ. "Systemic blood activation with open and closed venous reservoirs. Annals of Thoracic Surgery, 1995; Vol. 59, pages 1549–55) comparing the hard shell to the bag reservoir found significantly lower blood activation, shed blood loss, crystalloid infusion, and hemolysis, and less donor blood infusion with the bag reservoir. Schonberger's group recommended against routine use of an open (hard shell) venous reservoir system. Currently, a slight negative pressure applied to the venous line (to facilitate blood drainage) using a single pump can only be achieved with less desirable hard shell venous reservoirs. It is impossible to apply negative pressure to current soft-shell reservoirs, but it is possible with one preferred embodiment of the present invention.

In an open, hard shell reservoir, air escapes by floating to the top of the reservoir. In a bag reservoir, air floats to the top but must be actively eliminated. This can be done manually with a syringe, or more frequently with a roller pump operating slowly so as to continuously pump fluid to the cardiotomy reservoir. With either method, a sudden large volume of air can overwhelm the air removal system and cause disastrous consequences, especially without a vigilant perfusionist. With one preferred embodiment of the present invention, air would be eliminated automatically without a roller pump or intervention by the perfusionist, and priming of the extracorporeal circuit would be facilitated through faster air removal utilizing either a floating ball valve or a hydrophobic membrane. Currently there are devices used in the CPB circuit that incorporate hydrophobic membranes that remove air yet do not allow blood to cross (e.g. Model # AutoVent-SV, Pall Corp Glen Cove N.Y.). Studies with filters used in these applications have shown that the membranes clear air from water almost indefinitely (many days), even if high suction is applied, without reducing gas transfer rate over time. However, when the membrane is exposed to blood, especially when high suction is applied, a film forms on the membrane over time, causing a significant increase in resistance to gas flow. The present invention incorporates designs and means to reduce this problem and extend the life of the membrane when used with blood. Likewise, U.S. Pat. No. 3,849,071 shows a floating ball within a blood filter that supposed to open a purge port when air enters and close when the blood level rises. However, as described, it is a physical impossibility for the ball to "fall" and open the purge port because, as shown, the weight of the floating ball is insufficient to overcome the force holding the ball against the purge port. With the present invention, the relative weight of the ball, the internal diameter of the purge port, and the suction applied to the purge port are designed to assure that the ball will drop to open the purge port in response to air level in the venous reservoir.

With prior art soft-shell reservoirs, air may be trapped at the top of the liquid by the collapsed walls of the reservoir, see FIG. 1a. U.S. Pat. No. 4,622,032 illustrates a soft shell reservoir having an inlet tube extending from the bottom half way into the reservoir. Reference 13, sold by Johnson and Johnson (and later by Medtronic) shows a soft shell reservoir with an inline tube extending, along one side of the bag, to the gas purge port at a 45° incline. This design has a rigid fluid path between blood inlet and gas purge port. However, this design is not as conducive to air removal as a vertical fluid path would be. In addition, the tube extending between inlet tube and purge port had an ID of ⅝", or only 25% greater diameter than the inlet tube. Thus, the velocity of the liquid in the column slows to only 64% of the inlet velocity. In another aspect of the present invention, a vertical path is provided from the blood inlet at the bottom of the bag to the gas purge port at the top of the bag, such path limiting the aforementioned problem of trapped air. The vertical path also has a large enough diameter that slows the velocity of the liquid to at least 25%, and more preferably to at least 15% of the inlet velocity. As will be shown, lower blood velocity is more conducive to bubble removal.

State of the art soft shell venous reservoirs with a screen are designed such that a large portion of the screen contacts the internal walls of the bag, thereby increasing the resistance to blood flow across the screen, and rendering that portion of the screen ineffective, at least partially. This contact between the screen and the walls of the bag increases as the volume in the reservoir decreases. The present invention reduces that problem by preventing the external walls of the venous reservoir from contacting the screen.

The indication of blood level in present soft shell venous reservoir is very inaccurate and low level, or air-in-the-reservoir, alarms are not reliable because many are designed for hard shell reservoirs. The present invention provides effective means to alarm at low blood levels and in the soft shell venous reservoir.

Currently, at the end of the bypass procedure, the patient is weaned off the heart lung machine by reducing the bypass flow. This is achieved by partially clamping the venous line and decreasing the speed of the arterial pump. Once off bypass, the blood left in the venous reservoir is gradually pumped back to the venous side of the patient. Another aspect of the invention allows the user to adjust the positive pressure applied to the blood within the venous reservoir. By being able to increase the pressure of the venous reservoir, the user can effectively reduce venous drainage or perfuse the blood back to the patient. This is not possible with current venous reservoir bags and may be dangerous with hard shell reservoirs (i.e., air may be pushed to the patient).

The inventor has also previously described an inline bladder (The Better-Bladder™, see U.S. Pat. No. 6,039,078), a device with a thin walled, sausage shaped bladder sealed inside a clear, rigid housing. Since the bladder is made from a single piece of tubing, the blood path is smooth with no flow discontinuities. The bladder portion is sealed within the housing that has an access port to the housing space outside the bladder. Because of its thin wall, the enlarged section can easily collapse. Thus, it can serve as an inline reservoir, providing compliance in the venous line to reduce the pressure pulsations at the pump inlet. The Better-Bladder also transmits the blood pressure flowing through it across its thin wall, allowing pump inlet pressure to be measured noninvasively by measuring the gas pressure of the housing via the gas port. The degree of "gravity drainage" is user-adjustable by setting the negative pressure in the Better-Bladder housing. If the suction generated by the venous pump becomes too great, the pump is slowed or stopped by a pump controller. The Better-Bladder does not have a gas purge port or a screen to inhibit gas bubbles. It is also much smaller, having nominal volume of 80 ml for adult perfusion as compared to over 1,000 ml for a venous reservoir.

BRIEF SUMMARY OF THE INVENTION

The present invention incorporates improved designs for venous reservoirs that provide the benefits of prior art devices (limiting pump suction using the safer, pliable blood reservoir) while avoiding their disadvantages (air entrapment, inability to utilize VAVD, required vigilance for air removal). Further, its advantages and uniqueness are also enhanced by providing the user with means to adjust the degree of suction applied for venous augmentation and assuring that a greater area of the screen is effective in liquid transport.

Briefly, the present invention in its simplest form consists of a blood reservoir having at least one pliable wall, a blood inlet, a blood outlet, and a gas purge port. In one preferred embodiment, a first structure having tubular cross section and semirigid wall is placed above said inlet thereby providing a first path for undesirable bubbles entering the reservoir to move to the top where they are eliminated via said gas purge port. The first structure preferably has an effective cross section that is larger than the ID of said inlet tube thereby slowing any blood flow and allowing more favorable conditions (longer time, lower drag) for gas bubbles to float upward. The wall of the first structure is sufficiently rigid to prevent collapse of said pliable wall from blocking said first path. In another preferred embodiment, the pliable wall of the venous reservoir is sealed externally, forming a pressure chamber external to the venous reservoir. Controlled suction applied to said external chamber is transmitted across said pliable wall thereby controlling the negative pressure of the blood at which said pliable wall moves.

It is therefore the objective of the present invention to provide an improved venous blood reservoir with at least one pliable wall that provides a path for gas bubbles entering the inlet to move unhindered up to the gas purge port.

A further objective of the present invention is an improved venous blood reservoir, having at least one pliable wall, allowing the user to adjust the negative pressure applied to said pliable wall thereby allowing for augmented venous drainage.

A further objective of the present invention is an improved venous blood reservoir designed to maintain its external wall from contacting the screen material and thereby reducing the resistance to blood flow across the screen.

Yet another objective of the present invention is to incorporate a one way valve at the outlet of the venous reservoir, said valve preventing blood from being sucked into the venous reservoir when pressure at the outlet of the venous reservoir is positive relative to the liquid pressure in the venous reservoir.

Another objective of the present invention is to provide an improved venous blood reservoir with at least one pliable wall that when placed at the pump inlet, provides compliance that reduces pressure fluctuations at said pump inlet.

Another objective of the present invention is to provide an improved venous blood reservoir with at least one pliable wall that when placed at the pump inlet, provides automated means to eliminate air.

Another objective of the present invention is to provide an improved venous blood reservoir with at least one pliable wall and with a relatively large gas purge port, said port providing a more volumetrically effective gas purge, and one that is less traumatic to the blood.

Another objective of the present invention is to provide automated means to detect air in the venous reservoir and utilize said means to alarm the user or control the suction used to remove air from the venous reservoir.

Other objectives, features and advantages of the present invention will become apparent by reference to the following detailed description of the presently preferred, but nonetheless illustrative, embodiments thereof with reference to the accompanying drawings therein.

BRIEF DESCRIPTION OF THE DRAWINGS

FIG. 2b is a line drawing of a cross section taken of FIG. 2a along line 15–15'.

FIG. 2c is a line drawing of a cross section taken of FIG. 2a along line 16–16'.

FIG. 2d is a line drawing of a cross section taken of FIG. 2a along line 17–17'.

FIG. 2e is a line drawing illustrating the flow of blood and air at the inlet of the venous reservoir shown in FIG. 2a.

FIG. 2f is a line drawing illustrating one preferred method to assemble the screen used with the venous reservoir shown in FIG. 2a.

FIG. 3a is a line drawing illustrating one preferred sealing scheme of an adult size venous reservoir that allows the use of a universal holder for it and the pediatric venous reservoir shown in FIG. 3b.

FIG. 3b is a line drawing illustrating one preferred sealing scheme of a pediatric size venous reservoir that allows the use a universal holder for it and the adult venous reservoir shown in FIG. 3a.

FIG. 6a is a line drawing illustrating one preferred embodiment of the present invention where air removal is automated by utilizing a floating ball valve.

FIG. 6b is a line drawing illustrating another view of the bottom of the ball cage used in FIG. 6a taken along line 23–23'.

FIG. 6c is a line drawing illustrating another view of the ball cage used in FIG. 6a taken along line 24–24'.

FIG. 6d is a line drawing illustrating another embodiment of the present invention where air removal is automated by utilizing a floating ball valve incorporating two safety features.

FIG. 7a is a line drawing illustrating another preferred embodiment of the present invention where a rigid cylinder, incorporated as one external wall of the venous reservoir, maintains the screen wall unhindered and provides an uninterrupted fluid path between blood inlet and gas exhaust port.

FIG. 7b is a line drawing of a cross section taken of FIG. 7a along line 25–25'.

FIG. 7c illustrates rigid cylinder 72, shown in FIG. 7a, isolated and rotated 90° counter clockwise.

FIG. 7d is an enlarged view of the top, circled section of the venous reservoir shown in FIG. 7a illustrating the slot providing communication for removal of air external to the screen.

FIG. 7e is a line drawing of a cross section taken of FIG. 7d taken along line 26–26'.

FIG. 7f is a line drawing of a cross section taken of FIG. 7e taken along line 27–27'.

FIG. 8a is a line drawing illustrating one preferred embodiment of the present invention where a venous reservoir can be sealed within a rigid housing where suction can be applied to the external flexible walls of said reservoir thereby providing venous augmentation.

FIG. 8b is a line drawing of a cross section taken of FIG. 8a along line 28–28'.

FIG. 8c is a line drawing of a cross section taken of FIG. 8a along line 29–29' illustrating the rigid bottom cap used with the venous reservoir to seal the bottom of the housing shown in FIG. 8a.

FIG. 9a is a line drawing of another preferred embodiment of the present invention wherein the venous reservoir can be sealed within a rigid housing where suction can be applied to the external flexible walls of said reservoir thereby providing venous augmentation.

FIG. 9b is a line drawing of a cross section taken of FIG. 9a along line 30–30' showing the bottom seal of the venous reservoir within the housing and door shown in FIG. 9a.

FIG. 9c is a line drawing of a cross section taken of FIG. 9a along line 31–31' showing the top seal of the venous reservoir within the housing and door shown in FIG. 9a.

FIG. 9d is a line drawing of a cross section taken of FIG. 9a along line 32–32' showing another preferred sealing means incorporated into the inlet tube of the venous reservoir shown in FIG. 9a.

FIG. 9e is a line drawing of a cross section taken of FIG. 9d along line 33–33' showing a top view of the means incorporated into the inlet tube of the venous reservoir shown in FIG. 9a.

FIG. 9f is a line drawing identical to that shown in FIG. 9d except that this embodiment incorporates a gasket having an indentation to seal about the inlet tube of the reservoir, and a deeper indentation in the housing to support said tube while the venous reservoir is loaded.

FIG. 10a is a three dimensional rendering of another preferred embodiment illustrating an adaptation of the present invention to other venous reservoir having at least one flexible wall by sealing said flexible wall within a rigid housing such that suction can be applied externally to said flexible wall, thereby providing venous augmentation.

FIG. 10b is a line drawing of a longitudinal cross sectional view of FIG. 10a.

FIG. 10c is a line drawing of a cross section taken of FIG. 10b along line 10c–10c' showing another view of the venous reservoir within the housing shown in FIG. 10a.

FIG. 11 is a line drawing illustrating another embodiment of the present invention where air removal is automated by connecting the gas exhaust port of the venous reservoir to the inlet port of a cardiotomy reservoir, said cardiotomy having negative pressure applied to it.

DETAILED DESCRIPTION OF THE INVENTION

Figure 1:
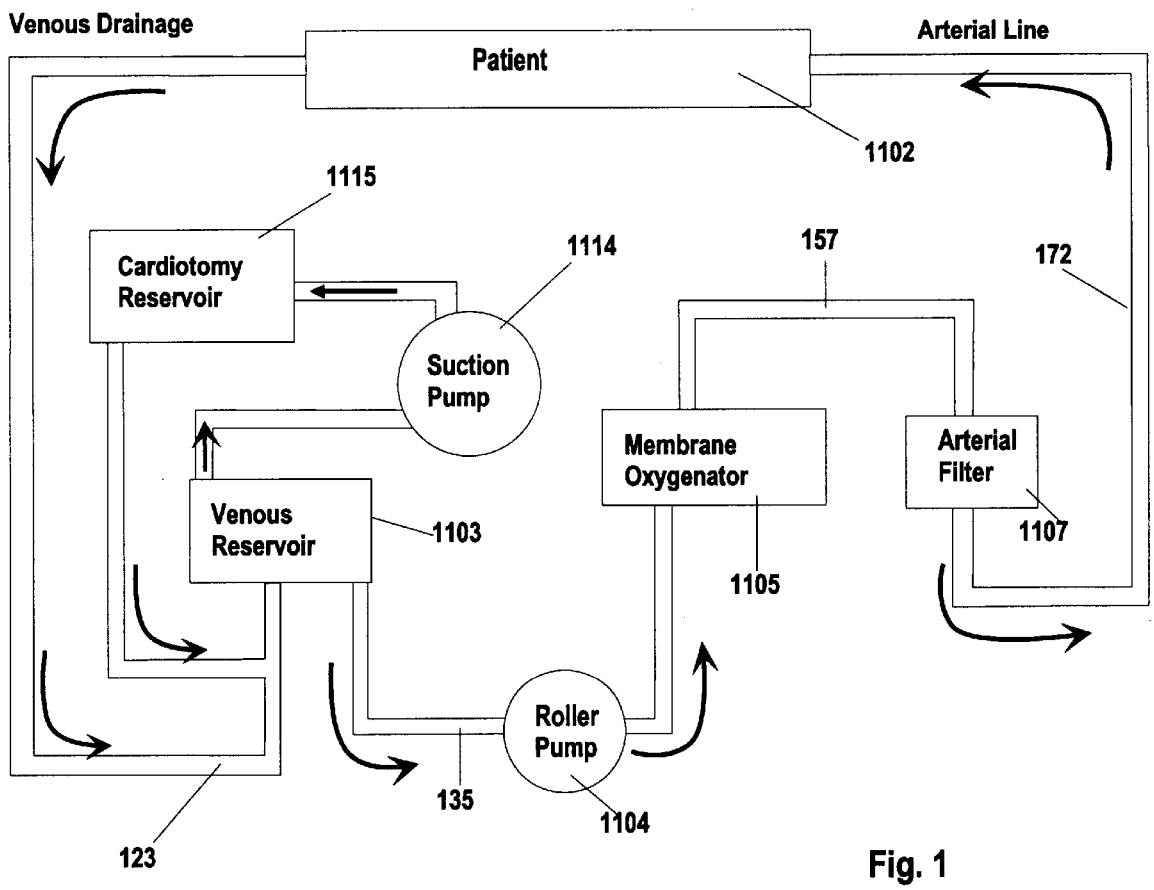
FIG. 1 is a line drawing of the pertinent components of a typical cardiopulmonary bypass (CPB) circuit showing the relative location of the venous reservoir of the present invention.
Figure 1A:
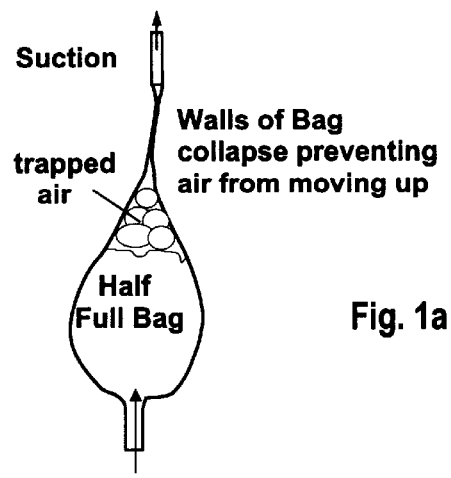
FIG. 1a is a line drawing of a typical prior art venous reservoir, illustrating how incoming air bubbles are prevented from reaching the gas exhaust port and are trapped midway in the bag.

Reference should now be made to the drawings wherein the same reference numerals are used throughout to designate the same or similar parts. It should be noted that the use of cardiopulmonary bypass, as shown in FIG. 1, is for descriptive purposes, and should not be taken as a limitation to the use of the devices described hereinafter. It should also be noted that the term soft shell reservoir, venous bag and bag hereinafter are used interchangeably.

FIG. 1 is a schematic representation of a system according to the present invention and showing the relative location of the venous reservoir in a typical cardiopulmonary bypass circuit. As shown, tubing 123 is inserted at one end by means of a cannula (not shown) in the vena cavae for obtaining venous blood from the heart (not shown) of patient 1102. Tubing 123 is coupled, as an example, to venous reservoir 1103. The blood is drawn from venous reservoir 1103 via tube 135 by roller pump 1104 and pumped through a membrane oxygenator 1105 wherein oxygen is supplied to the blood and carbon dioxide is removed. The blood from the oxygenator is then conducted by means of tubing 157 to arterial filter 1107 and then via tubing 172 and an arterial cannula (not shown) back to the patient. As described in the prior art, the venous blood, here shown coming from the patient's vena cavae, may contain air that must be eliminated before it is pumped back to the patient. This is one of the main functions of the venous reservoir. As shown, air entering venous reservoir 1103 rises to the top of said reservoir where it is removed by suction pump 1114 to cardiotomy reservoir 1115. Roller pump 1104 is usually one of 3 to five pumps composing a heart-lung machine, which is part of a hardware required for cardiopulmonary bypass.

FIGS. 2a, 2b, 2c, 2d and 2e illustrate line drawings of one preferred embodiment of the present invention. Here, venous blood enters the venous reservoir 1819 via inlet tube 1 and is directed into first inlet chamber 2, shown as a cutaway. First inlet chamber 2 preferably has a circular cross section with its walls formed of fine screen 3 typically having a pore size of 40$\mu$ to 150$\mu$ and having an effective open area that is preferably greater than 40%. It is understood that though lower pore sizes result in higher resistance to blood flow, they prevent smaller bubbles from crossing the screen. It should also be understood that screen 3 is preferably heparin coated, to increase wettability and reduce clot formation. The top of chamber 2 is in fluid communication with gas purge port 4. The bottom of chamber 2 is open and is in fluid communication with inlet tube 1 and, via expandable chamber 8, with outlet tube 5. Preferably outlet tube 5 is located on the opposite side of, and lower than, inlet tube 1.(Bentley patent?)

Figure 2A:
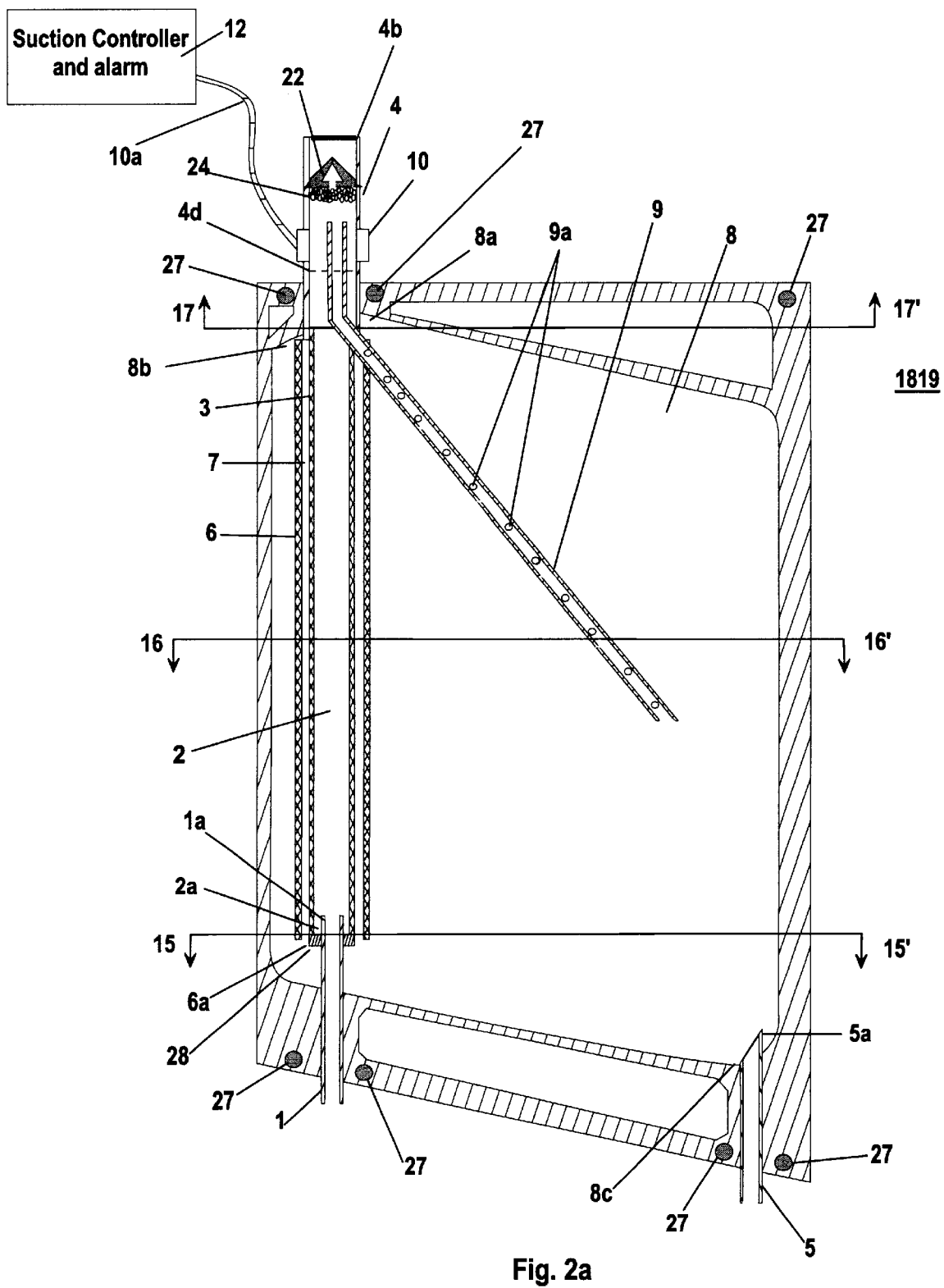
FIG. 2a is a line drawing illustrating one preferred embodiment of the present invention where a perforated cylinder is used to keep the flexible walls of the venous reservoir bag away from its screen as well as provide an uninterrupted fluid path between blood inlet and gas exhaust port.

In one of the preferred embodiment, shown in FIG. 2a, first inlet chamber 2 has a larger inside diameter than inlet tube 1 (e.g. 1.0" v. 0.5"), said larger diameter serves to slow the velocity of the blood (e.g. ¼ the inlet velocity), and thus allow more time for any bubbles to rise to the top where they can be removed. Slowing the blood also reduces the tendency of the flowing blood to carry the bubbles, especially the smaller ones, by reducing the drag on the bubbles by the moving blood. Lower velocity also lowers the tendency of larger bubbles to break into smaller ones; larger bubbles have a higher buoyancy and less of a chance of crossing screen 3 into expandable chamber 8, and flowing out of the bag through outlet tube 5 shown in FIG. 2a. With sufficient pressure across screen 3, the bubbles could cross into chamber 8 and travel to outlet 5 of the reservoir, a very undesirable outcome. To reduce that possibility, inlet chamber 2 is open at the bottom where debubbled blood can exit first inlet chamber 2 at 2a. To improve flow conditions, the outlet of inlet tube 1, 1a, is preferably centered with the centerline of chamber 2, as also shown in FIG. 2b (cross-section 15–15' in FIG. 2a). Also shown is one preferred embodiment of structure 28 that centers inlet tube 1 within chamber 2 formed by screen 3. Connector 28, shown in FIG. 2a and as a cross section taken of FIG. 2a along line 15–15' shown in FIG. 2b, lines up and connects inlet tube 1 to inlet chamber 2. Thus, in one preferred embodiment, connector 28 has a wheel cross-section with an internal circular structure 28a connected via spokes 28b to an external circular structure 28c. The inside diameter of inside structure 28a that allows interference fitting to the outside diameter of inlet tube 1 and the outside diameter of outside structure 28c supports cylinder 6. The space between internal structure 28a and outside structure 28c maintained by spokes 28b forms a fluid communication between inlet chamber 2 and expandable chamber 8 as indicated by the downward facing arrow at the bottom of FIG. 2e. It should also be obvious that since screen 3 may be flimsy, it may need radial support, as for example internal cage 26, see FIG. 2c (cross section 16–16' in FIG. 2a) and 2f. Screen 3 can be attached to cage 26 by various means (e.g. insert molding) longitudinally and radially to 26a or 26b and longitudinally to ribs 26c, for example by adhesive. This would maximize the ID of first internal chamber 2 to provide a smooth and straight vertical flow path thereby facilitating the upward motion of the bubbles.

With this design, as is the case for present venous reservoir bags (e.g. Bentley, Cobe, Sarns/3M, Minntech) most of the incoming blood would exit via screen 3 across which very few bubbles, if any, cross. However, present venous reservoir bags are made of four layers: the two outside layers being flexible PVC sheets and the two inside layers being a screen (e.g. U.S. Pat. No. 4,734,269). The screen is usually folded over with the fold being in the center of the venous reservoir bag and its edges sandwiched and sealed along at least two of edges of the two PVC outer layers. This design is simple but it provides no means to keep the internal surface of the external PVC walls from contacting the external wall of the screen. This contact reduces the effective screen area available for blood flow, especially at low blood volumes, causing further problems because more bubbles cross the screen at lower blood volumes. For example, tests conducted with the Cobe venous reservoir bag (Model # VRB, Cobe Lakewood, Colo.) showed that at a blood flow of 4.0 L/min and an air flow of 750 mL/min, the bubble count (size>50$\mu$) with a blood volume of 750 ml in the bag was 35 bubbles/sec as compared to 94 bubbles/sec when the blood volume was 500 ml. The Baxter venous reservoir bag (Model # BMR-1900, Baxter/Bentley Irvine, Calif.) had similar results: the bubble count increased from 69 bubbles/sec to 160 bubbles/sec when the blood volume decreased from 750 to 500 ml.

The present invention eliminates the problem of screen to wall contact by introducing means to maintain the wall of the venous reservoir bag away from the screen as well as to maintain a vertical column of blood within first inlet chamber 2. This can be achieved by either incorporating the means into the disposable bag, or by interfacing a disposable bag with a nondisposable holder, the combination providing the aforementioned means. FIG. 2a illustrates one preferred embodiment of the disposable type. Here, a semi rigid cylinder 6 with perforated wall is placed over screen 3 forming second inlet chamber 7 in fluid communication with expandable chamber 8 via said perforations as well as its open bottom at 6a. The perforations can be effectively formed by using a tubular net with, for example 0.030" to 0.100" diameter strands forming a diamond shaped opening, see 6 in FIG. 2a, and can be obtained from Nalle Plastics Inc. Austin, Tex. The tubular net can be made of polypropylene, polyester, Nylon, or polyethylene. It must possess at least three properties: 1) sufficient stiffness (either by rigidity of the material or thickness of the yarn) and structure to keep walls 18 and 19 (FIGS. 2*b*, 2*c*, 2*d*) of venous reservoir bag 1819 (FIG. 2*a*) away from screen 3 thereby maintaining chamber 7; 2) an opening to allow unhindered fluid communication between chamber 7 and expandable chamber 8; and 3) cause no undesired interaction with biological fluids. Tubular net 6 preferably extends vertically from the bottom of venous reservoir 1819 at its inlet to the top of said reservoir and can be attached to the external wall of air-venting tube 4 for support. The inlet to cylinder 6, 6*a*, may extend below screen 3 providing free fluid communication between inlet 1 and expandable chamber 8. With this design, experiments similar to those described for the Cobe and Baxter bags result in a steady bubble count of 60 at bag volumes of 500 and 1000 ml.

FIG. 2*e* illustrates the blood path of the present invention. Venous blood with some gas bubbles 23 enters the venous reservoir via inlet tube 1. The inertial forces of the blood exiting outlet of tube 1 propel the blood and bubbles upward into first inlet chamber 2. Chamber 2 is lined up within ±15° of the vertical line. This essentially vertical position, unlike prior art devices, provides the least resistance for gas bubbles to rise up chamber 2 to air-venting tube 4 where they are evacuated by suction applied to the outlet of tube 4, port 4*b*.

As shown in FIG. 2*a*, screen 3 extends to the top of venous reservoir 1819 where it is sealed to air-venting tube 4. This seal prevents blood from exiting at the top where it may drag bubbles out of inlet chamber 2 into expandable chamber 8. Should gas volume increase at tube 4 and displace blood volume at the top of chamber 2, the gas could cross screen 3 and enter chamber 7 and chamber 8. Because screen wall 3 may get wet again before all the gas at the top of chamber 8 is removed, that gas can be trapped. Purge tube 9 (see FIGS. 2*a* and 2*e*) is provided to allow gas to be purged from chambers 7 and 8. For that purpose, the topmost entry point of tube 9 into chamber 8 is the highest point in chamber 8 (e.g. point 8*a* is higher than point 8*b*). Tube 9 extends from air-venting tube 4 into chamber 8, said extension preferably having holes 9*a* in its wall to provide better fluid communication with chamber 8 along the entire length of tube 9. Holes 9*a* allows air to enter tube 9 and be evacuated as described before. Other holes may be punched into tube 9 to allow air to be evacuated at any blood level. The smaller diameter of tube 9 and the location of its outlet at the top of venting tube 4 reduces the chance of blood flowing (with bubbles) from chamber 2 to chamber 8 via tube 9. As well known in the art, tube 9 can alternatively be sealed directly into chamber 8 and external to air-venting tube 4. As shown, tube 9 is exposed to the same suction applied to air-venting tube 4.

With the present invention because, air moves freely to the top of bag 1819 where it can be purged easily. It therefore should be obvious that the degree of suction applied and the blood volume removed in order to purge the gas should be significantly lower than with present devices. The smaller blood volume removed, the lower flow required to remove the gas and the larger ID of the purge line all contribute to significantly lower blood damage. This is especially true when stopcocks, which have very small ID (e.g., 0.062" and sometimes less) and are used with present devices, are eliminated.

The user may not easily determine the presence of bubbles or the blood level in first inlet chamber 2 due to the opacity of the blood and/or screen 3. Yet another innovation provides means to easily ascertain the presence of bubbles by increasing the ID of air-venting tube 4 to at least ¼" but preferably ⅜" or greater. Other venous reservoir bags have gas ports of ⅛" ID or smaller, which presents a high resistance to gas and blood flow. The increased port diameter of the present invention increases the case by which bubbles rise up tube 4 for two reasons. First, gas bubbles move up easier in a liquid filled tube having a diameter larger than the diameter of the bubbles. Second, a larger diameter tube accommodates larger bubbles with greater buoyancy, providing greater upward force on the bubbles relative to the capillary force within a liquid filled tube that inhibits their movement. Thus, by having an exhaust tube with a larger diameter, the user could pull blood up into tube 4. Should air enter first inlet chamber 2, it would travel up and replace the blood in tube 4 causing the visible blood level 4*d* (see FIG. 2*a*) in tube 4 to drop, an indication that air entered the venous reservoir and must be removed. It should be understood that the process can be automated by incorporating level detector 10 radial to air venting tube 4, said detector 10 connected to a suction controller and/or alarm monitor via transmitter line 10*a*. Monitor/controller 12 alarms the user to air entering tube 4 and/or starts the required suction applied to the outlet of tube 4, 4*b*, to remove said air and raise the liquid level. Once the level detector detects the rising liquid, it can stop the alarm and/or stop the suction used to remove the gas from the venous reservoir. Monitor/controller 12 can, for example, control the speed of the pump providing suction. Alternatively, it can open or close the tube providing suction (not shown) by a solenoid actuated tubing clamp.

Also, as described in reference to one way valve 422 in reference to FIG. 4, preferably one-way valve 22, placed just below outlet 4*b* of tube 4, prevents air from entering the reservoir if the reservoir empties and is exposed to the suction generated by arterial pump 1104. Further, defoamer sponge 24, preferably incorporating anti-foam A and placed below valve 22, may be used to break up blood in the form of foam that reaches the inlet of valve 22. Placement of defoamer 24 at the top of tube 4 provides the desirable defoaming action while limiting contact between the defoamer and the blood that rises to that level.

As shown in FIG. 2*a* the large diameter of chamber 2 allows more time for the bubbles to rise to the top and causes less turbulence that could hinder the upward motion of the bubbles. Most of the blood preferably flows from chamber 2 to chamber 7 across screen 3, thereby assuring the upward motion of the bubbles. This preference is enhanced by cylinder 6 maintaining screen 3 free of contact with venous reservoir walls 18 and 19, see FIG. 2*c*. Typically, if wall screen 3 forms a cylinder with a 1" diameter, then for an 8" high structure, its surface area is 25in2. This large effective area is available for blood flowing from inlet chamber 2 to expandable chamber 8 and is virtually independent of the blood volume in expandable chamber 8. Annular space 7 formed by cylinder 6 and screen 3 and better seen in FIG. 2*c*, serves to separate gas from the blood; any bubbles that may have crossed wall 3 can still be buoyed upward to the top of chamber 7 where they can be removed by tube 9. The blood then flows from expandable chamber 8 to outlet port 5. Should air enter chamber 8, it can still float to the top of said chamber and be eliminated via tube 9. Thus with this design, there are three chambers for air elimination: chambers 2,7, and 8.

A major reason a collapsible bag is used as a venous reservoir is to prevent air from being pumped out of the bag and into the patient should the venous reservoir empty. In present bags this is achieved by having the outlet port (5 in FIG. 2*a*) at the lowermost point of the bag. This can be incorporated into the present invention. Alternatively, the inlet of outlet tube 5, 5*a*, can be cut on a diagonal (nominal 35° to 65°) with its pointed end protruding into expandable chamber 8 and its low point in line with the periphery of the bag at 8c, as shown in FIG. 2a. Tube 5 should be made of relatively soft material (e.g. 55 Shore A) and have a relatively large ID/wall ratio (e.g. 0.5"/0.062"=8). Since a larger ID/wall ratio, as well as softer durometer wall, requires a lower pressure difference across the wall of the tube to collapse the tube, then the combination of higher ratio and lower durometer can be used to quantify the ease of said collapse, (ID/wall)/durometer. Thus, for the above example, (0.5"/0.062")/(55)=0.147. This number is significantly higher than that obtained for the outlet tube typically used at the outlet of present venous reservoirs (0.5"/0.093")/(65)= 0.082. Since the ease of tube collapse is related to (ID/wall)$^3$, (see my U.S. Pat. No. 5,215,450: Innovative Pumping System for Peristaltic Pumps), even a small change in that ratio causes a large change in ease of collapse. Thus, the softer tubing and/or high ID/wall ratio allows collapsing walls 18 and 19 of venous reservoir bag 1819 to gradually, rather than suddenly, impede the flow out of outlet tube 5. Once empty of liquids, the present aspect of the invention provides a looser seal about the outlet as compared to standard bags. Thus, when inlet flow resumes, less volume is needed to open the outlet tube, thereby providing resumption of flow sooner than present venous reservoir bags.

An experiment was conducted to determine the negative pressure developed between the outlet of venous reservoir 1103 and the inlet of pump 1104 when pump 1104 (see FIG. 1) was pumping at 6.0 L/min out of venous reservoir 1103 and the venous flow into the venous reservoir was less than 6.0 L/min. The reservoir was emptied and its outlet collapsed. Also measured was the blood volume required in the venous reservoir to reopen the venous reservoir outlet. Once emptied, the outlet of the Cobe reservoir bag stayed closed until the volume in the bag increased to over 1,400 ml. During that time, the pump inlet pressure (measured in line 135 in FIG. 1) decreased to and remained at over −600 mmHg. Once the blood volume in the bag reached 1,400 ml, sufficient pressure was exerted to expand walls and release the collapsed outlet of the venous reservoir, thereby allowing resumption of blood flow from the venous reservoir to the pump inlet. A similar experiment with the Baxter bag required an increase in blood volume of 400 ml before the high negative pressure at the pump inlet (−580 mmHg) was relieved and the bag outlet opened up. With the present invention, only 350 ml were required to open the venous reservoir outlet and reestablish flow, and the maximum negative pressure was only −400 mmHg.

As shown in FIGS. 2a, 2b, 2c, 2d, layers 18 and 19 are heat sealed (e.g., by radio frequency welding) by a double margin along their upper and lower edges, by a relatively wide seal along their right edge and by a narrower seal along their left edge. Anchoring holes (eyelets) 27, used to hang bag 1819, can be formed by punching holes through, and along, the top and bottom of the heat sealed surface. The preferred configuration includes a hole on both sides of inlet tube 1, outlet tube 5, and air-venting tube 4, and in the upper corner of the bag opposite tube 4 to facilitate secure attachment of the bag to the frame, see FIG. 2a.

Figures 3A, 3B:
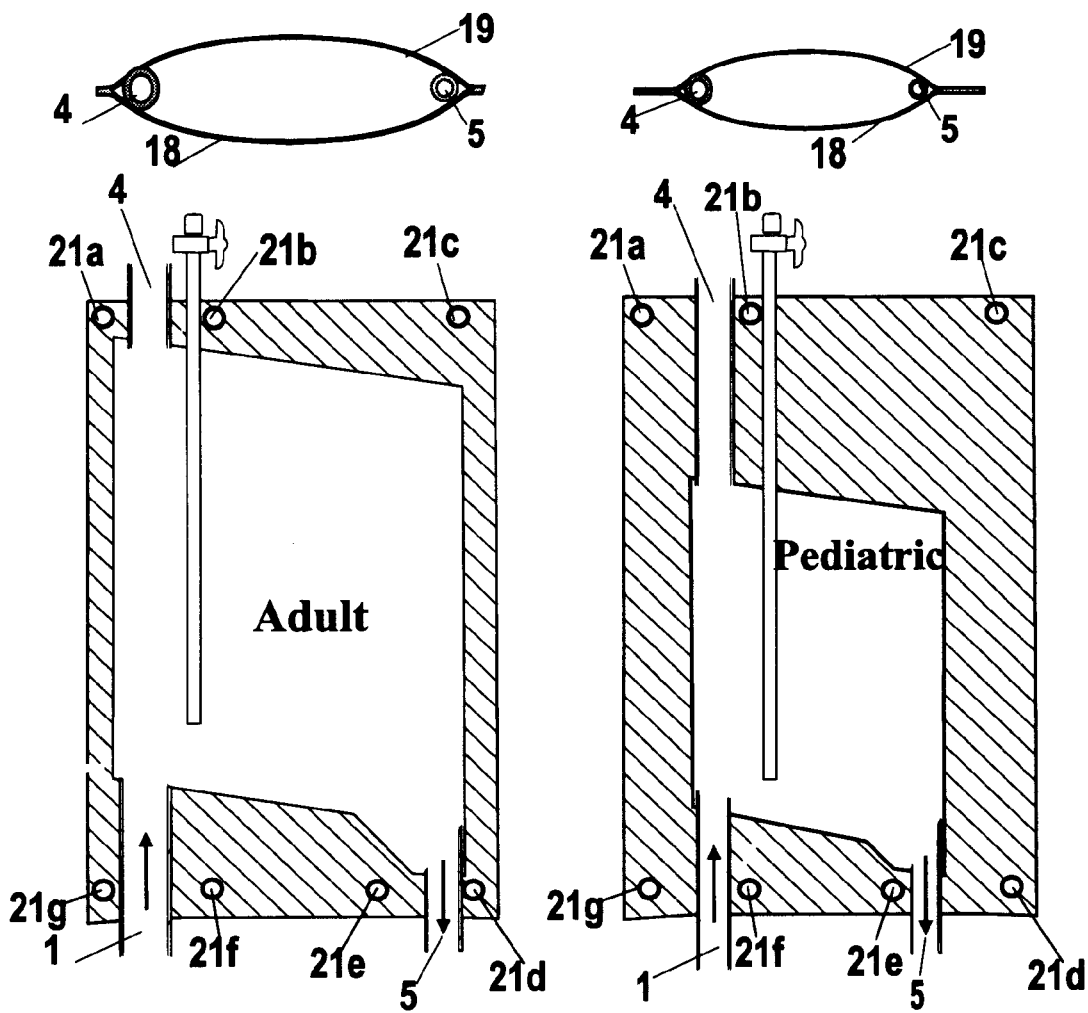

It should be understood that various sizes of the venous reservoir can be made without necessarily affecting their performance; for example, three popular sizes having capacities of 400, 1200, and 2000 ml are some of the possibilities. To simplify manufacturing and reduce costs of the hardware, all reservoir sizes can have the same footprint so each size can utilize the same frame. Here, smaller capacity reservoirs have a smaller bag portion and larger peripheral area (FIGS. 3a and 3b). Anchoring holes 21a, 21b, 21c, 21d, 21e, 21f, and 21g used to attach each bag to the frame can be accommodated by corresponding adjustable supporting pins in the frame, for example, as well known in the art.

FIGS. 7a, 7b, and 7c illustrate another preferred embodiment of the present invention. Here, rigid cylinder 72 replaces perforated cylinder 6, shown in FIG. 2a, to provide annular space 77 as well as to serve as part of the wall of venous reservoir 772. Pliable venous reservoir walls 18 and 19 are sealed to rigid cylinder 72 on both sides of longitudinal slot 72a, said slot better seen in FIG. 7b (a cross sectional view of cylinder 72 along lines 25 and 25' in FIG. 7a) and 7c (a cross sectional view of cylinder 72 along lines 272 and 272' in FIG. 7a), providing fluid communication between annular space 77 and expandable outlet chamber 8. To reduce stasis and provide smooth blood flow, the incline at the bottom of the rigid cylinder 72, 72d, matches the bottom incline of chamber 8, 8d. Cylinder 72 (FIG. 7b) preferentially has longitudinal lips 72b and 72c along both sides of slot 72a, said lips tapering and thinning as they extend outward. These lips serve to seal venous reservoir walls 18 and 19 about slot 72a (e.g., by radio frequency welding) as well as to form a smooth blood flow path from annular space 77 to expandable chamber 8. It should be obvious that cylinder 72 preferentially is made of biocompatible, clear, rigid thermoplastic that can be easily sealed to venous reservoir walls 18 20 and 19. A good choice would be rigid PVC. It should be obvious that screen 3, air-venting tube 4, outlet tube 5, and expandable chamber 8 formed by walls 18 and 19 serve the same purpose described for the venous reservoir embodiment shown in FIG. 2a.

FIG. 7d, which is an enlargement of the circled section shown in FIG. 7a, illustrates another preferred embodiment providing a fluid path between chamber 8 and air-venting tube 74 that allows air removal present in annular space 77 and expandable chamber 8. Here, cylindrical air-venting tube 74 has a notch 74h, at its bottom, also seen in FIG. 7e, which is a view of FIG. 7d taken along cross section 26–26' and FIG. 7f, which is a view of FIG. 7e taken along cross section 27–27'. As shown, the height of notch 74h extends beyond the top of screen cage 26, 26b. As previously described in reference to FIG. 2c (cross section 16–16' in FIG. 2a) and 2f, 26b and 26a in FIG. 7a, 7b, and 7d are the top and bottom respectively of the internal screen cage 26 which also may include ribs 26c. The bottom of notch 74h extends onto the highest point of chamber 8, 8a, which also preferentially corresponds to the highest point of screen 3. Thus, notch 74h provides a fluid communication, see arrow 84 in FIG. 7d, between air-venting tube 74 and chamber 8. Notch 74h replaces the function of tube 9 shown in FIG. 2a.

As described so far, air removal is accomplished as it is by current techniques: suction pump 1114 (see FIG. 1) typically with ¼" ID tubing is used to remove the gas from the top of the venous reservoir. This arrangement works but requires constant vigilance and intervention by the user to control air removal. Another innovative feature of the present invention is that air can be automatically eliminated from the reservoir with little or no user intervention required. Three preferable designs for the air purge port use a hydrophobic membrane, a floating ball, or controlled suction. All three methods allow air to be removed with very little, or no blood loss. The user would have the option to connect wall suction or one of the sucker pumps as the suction source for the air purge port, preferably having some regulating means to adjust/limit the degree of suction.

Figure 4:
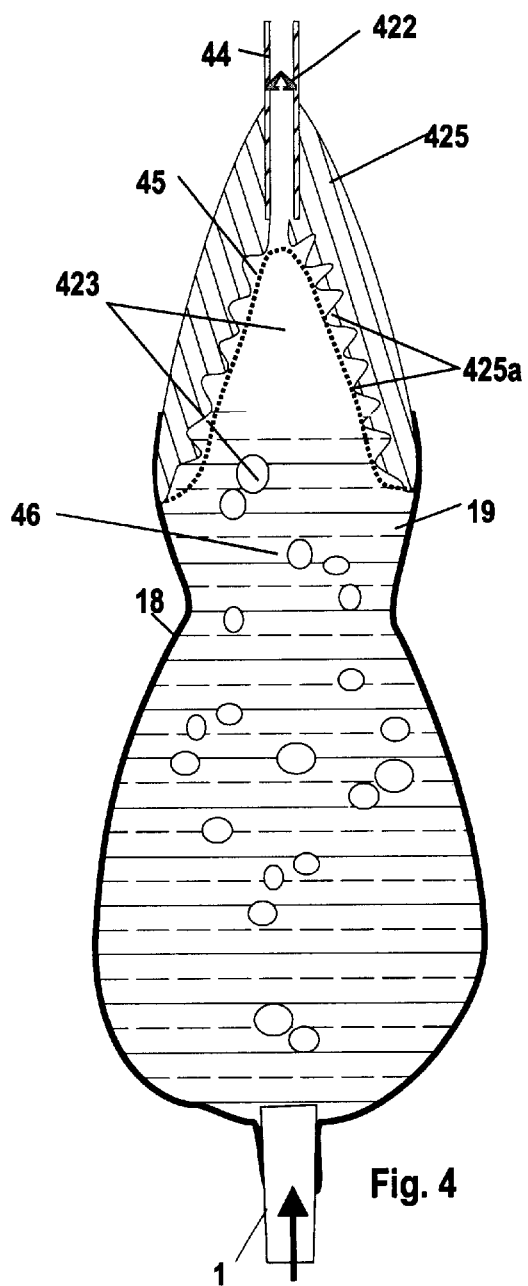
FIG. 4 is a line drawing illustrating one preferred embodiment of the present invention where the venous reservoir is topped with a microporous membrane that allows air, but not blood, to be removed.

FIG. 4 illustrates one preferred embodiment that achieves a large membrane area at the top of the venous reservoir. The design, with a cross section in the shape of an inverted "V" or "U", achieves a large area and provides an inclined surface. Membrane 45 has an inclined surface that facilitates clearing of any blood film off the surface of the membrane. Gravity and wicking should encourage any such film to "peel" off the surface into the blood pool, thereby maintaining the membrane clearer and the gas transfer rate up. Membrane support 425 can be incorporated as the top of a semi-rigid PVC frame formed into a protective "roof". The inside surface of the roof-contacting membrane incorporates ridges 425a, which are in unimpeded fluid communication with air-venting tube 44. Ridges 425a also support membrane 45 and prevent it from deforming due to pressure differences across its wall. The membrane should meet a high gas flow elimination requirement (at least 1 L/min at −100 mmHg). Membranes preferably are made of PTFE (e.g. Durapel™ from Millipore, Bedford, Mass.) or polypropylene (e.g. Zintex™ from WL Gore, Elkton, Md.), preferably having a pore size between $0.45\mu$ and $1.0\mu$. The small pore provides a sterile barrier.

The membrane is used to remove air 423 automatically from the top of the venous reservoir by applying suction (from the hospital supply) to air-venting tube 44. Hydrophobic microporous membrane 45 prevents the loss of blood 46 from the venous reservoir. One-way valve 422 may be placed at the outlet of air-venting tube 44 to prevent air from entering the reservoir if the reservoir empties and is exposed to the suction generated by arterial pump 1104. Membrane 45 has sufficient surface area to allow the removal of the expected volume of air entering the venous reservoir. Studies have shown that membranes that clear air from water can function almost indefinitely (many days) and high suction can be applied without reducing gas transfer rate over time. (However, over time, when the membrane is exposed to blood, especially when high suction is applied, a film overlays the membrane, resulting in a significant increase in resistance to gas flow. When applying lower suction (preferably between −50 and −200 mmHg), the transfer rate of gas across the membrane does not decrease as fast as with high suction (possibly due to less plasma penetration into the pores or lower holding force of the film). Therefore, removing air from blood requires a membrane with a larger area. The larger area compensates for the lower suction used to extend the life of the membrane and the lower transfer rates seen with blood as compared to water.

Figure 5A:
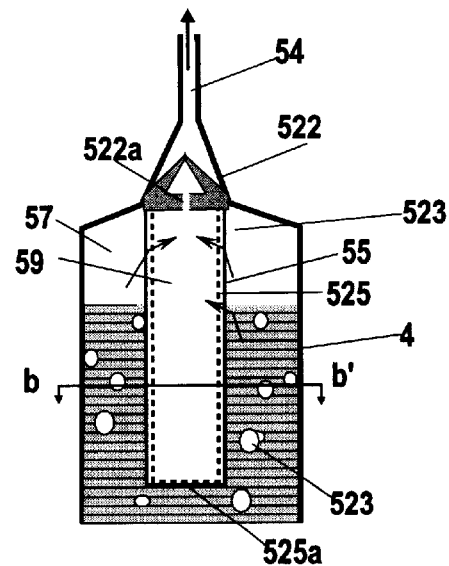
FIG. 5a is a line drawing illustrating another preferred embodiment of a microporous membrane placed at the top of the venous reservoir allowing air, but not blood, to be removed.
Figure 5B:
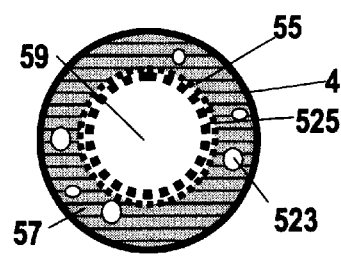
FIG. 5b is a line drawing of a cross section taken of FIG. 5a along line b–b'.

Another preferred embodiment, shown in FIGS. 5a and 5b, utilizes a tubular microporous membrane 55 in fluid communication with purge port 54, said tubular membrane internally supported and sealed to perforated rigid housing 525. Perforated rigid housing 525 allows gas to cross membrane 55 and enter chamber 59 unimpeded. Housing 525 is sealed at the bottom along 525a. Chamber 59, formed by housing 525, is in fluid communication with purge port 54. Annular space 57 is formed by circular membrane 55 and air-venting tube 4. Air-venting tube 4 could be in fluid communication with first inlet chamber 2 shown in FIG. 2a and preferably located on top of chamber 2. Normally annular space 57 is filled with blood. Should air 523 enter line 1 (see FIG. 2a), it would rise up chamber 2, as shown in FIG. 2e, enter annular space 57 (FIGS. 5a and 5b,) across membrane 55 into chamber 59 (FIG. 5a), across port 522a of one-way valve 522, and be purged via purge port 54. Applying suction to purge port 54 facilitates air removal by increasing the pressure difference across membrane 55. As described in the "roof" design referenced in FIG. 4, vertical placement of tubular membrane 55 facilitates "peeling" of the blood layer of the surface of the membrane, thereby improving long-term gas transfer.

The second preferred method to remove air utilizes a floating ball, which allows air but not blood to be removed through the purge port. As shown in FIG. 6a, housing 64a forms chamber 67 that allows air bubbles to rise unhindered as previously described for chamber 2 and tube 4 in reference to FIG. 2a. Housing 64a incorporates ball cage 68, floating ball 61 and unidirectional valve 622. Port 622a of unidirectional valve 622 providing fluid communication between chamber 67 and gas exhaust port 64, is open as long as air 623 is present in chamber 67. When most of the air has been eliminated, the rising fluid level brings ball 61 to the top of chamber 67, effectively closing port 622a. In this position, any further withdrawal of fluid from the venous reservoir is prevented. When more air enters the reservoir, the blood level falls, ball 61 drops, and the applied suction removes air 623. Suction may be provided by a wall source or a suction pump, but preferably is controlled for the purpose described below.

There are two forces maintaining ball 61 up against port 622a keeping said port closed: the buoyancy of the ball and the suction force applied at the gas port (Fs). $Fs=(\pi d2S/4$, where d is the inside diameter of air port 622a in contact with ball 61, and S is the negative pressure (suction) applied via air venting tube 64 against said ball. The upward force, Fs, must be less than the weight of the ball so that when the blood level drops, the weight of the ball overcomes Fs and the ball falls. Cage 68, in general has a larger ID than the OD of ball 61, see 68a in FIGS. 6a and 6c, where FIG. 6c is a line drawing illustrating another view of the ball cage used in FIG. 6a taken along line 24–24'. Cage 68 aligns the ball with air port 622a. The bottom of cage 68 narrows down to an ID smaller than the OD of ball 61, see 68b FIGS. 6a and 6b, where FIG. 6b is a line drawing illustrating another view of the bottom of the ball cage used in FIG. 6a taken along line 23–23'. The smaller ID 68b serves to retain ball 61 within its chamber 67 and prevents it from falling into the venous reservoir. For this design, for example, ball 61 may be a 1" solid polypropylene ball (specific gravity sp=0.90), or a hollow ball (where sp is adjustable). Air port seal 622a could, for example, be made of soft silicone and the ID of the air port may be $\frac{1}{32}$". To assure a good seal, the surface of the ball should have a fine finish, preferably with a tolerance of 0.001" or better. The applied suction should be low to assure that ball 61 does not "stick" to gas port 622a in the closed position, and to minimize blood damage. For example, a pressure of −50 mmHg can be applied to remove the air. This degree of suction is sufficient to withdraw the air and maintain the liquid column within first and second inlet chambers 2 and 7 when flexible chamber 8 is less than full, see FIG. 2a. To prevent excess suction (e.g. over −150 mmHg) from being applied, the line between air-venting tube 64 and the suction source can include a t-connector 64c with a suction regulating valve 632 attached at the inlet of side port 64c (FIG. 6d). Such valves are commercially available at various cracking pressures and are currently used for IV infusion sets (e.g., NP Medical, Clinton, Mass., cost<$0.25). As well known in the art, a blood trap (not shown) may be incorporated so any blood that may enter the line would not progress to the suction source, and, in fact, excess lost may be returned to the patient. Alternatively, the air-venting tube 64 may be connected at 64b to Cardiotomy reservoir 1115 (see FIG. 1), to which suction is applied. Thus, any blood that may pass the ball valve system would go back to the patient via cardiotomy 1115. Safety is paramount. Therefore, side port 64d, having for example a female Luer, in fluid communication with first inlet chamber (e.g., via chamber 67 located within liquid column 66 in FIG. 6d), is placed prior to either the ball or the membrane. Port 64d provides the user means to eliminate incoming air in a fashion similar to that of present devices, in case the membrane or ball malfunctions.

Another preferred method to remove air is a variation of the second method but without the floating ball valve combination. As shown in FIG. 11, the top of first inlet chamber 112 of venous reservoir 113 is extended into "chimney" 114 that serves to vent air and is connected to cardiotomy reservoir 15, to which suction is applied at 15a. The degree of suction should be sufficient to elevate the blood level into chimney 114, even when the expandable chamber 118 is less than full. Thus, any air 623 entering inlet tube 111 would float to the top of first inlet chamber 112 and enter chimney 114. The air would then displace the liquid in chimney 114, coalesce with air volume 114a that interfaces between the blood in chimney 114 and outlet 114b of chimney 114, and the additional suction would pull the liquid up the chimney to its original level. This system requires that chimney 114 have an ID that facilitates upward movement of air bubbles, even large ones. The length of the chimney needs to be at least equal to the expected level of liquid column 66 when suction is applied to chimney 114 and expandable chamber 118 is full. Beyond that height, the outlet of chimney 114b can be connected, via ¼" ID tube 116, to cardiotomy reservoir 15. Air space 114a below chimney outlet 114b assures that the blood does not enter smaller diameter tube 116. Suction, applied at 15a, can be provided by the wall source, or suction pump 1114 (FIG. 1) connected to cardiotomy reservoir 15, said suction regulated to appropriate levels as well known in the art. Preferably outlet tube 115 of reservoir 113 is located on the opposite side of, and lower than, inlet tube 111.

As described in the Description of the Prior Art, improved venous drainage can be achieved by applying some negative pressure on the venous blood. Another aspect of the invention allows the user to apply suction with a collapsible reservoir. FIGS. 8a, 8b, and 8c illustrate venous reservoir 772, previously described in reference to FIGS. 7a, 7b, and 7c, placed in generally elliptical, clear rigid, housing 88. Housing 88 is open both at its bottom, defined by border 88a, and at its top, defined by border 88b, said borders having sealing gaskets 82 and 81 respectively. Disposable venous reservoir 772 incorporates rigid bottom cap 89, said cap having lip 89c with its inside diameter matching outside diameter of housing 88 to form a seal along gasket 82. Bottom cap 89 also is sealed to inlet tube 1 at 89a and outlet tube 5 at 89b. A similar arrangement is made at the top of venous reservoir 772 where rigid disk 72d is sealed along top gasket 81 of housing 88. Thus, the user would slip chimney 74 of disposable venous reservoir 772 into the bottom of housing 88, push it up and insert it through opening 88d at the top of housing 88. When lined up, rigid disk 72d is pushed against gasket 81 and bottom cap 89 seals against gasket 82. The bottom and top seals are reinforced and maintained by cap 89 held against housing 88 by snaps 88e, 88f, 88g and 88h that lock onto ridge 89d of cap 89. At the end of the case, snaps 88e and 88f shown in FIG. 8b, and snaps 88g and 88h shown in FIG.8a, each of which is hinged at its midpoint (e.g. see 88i of hinge 88f) are pushed inward, as shown by respective arrows 812 and 811 for snaps 88f and 88e, causing the bottom of said snaps (e.g. 88j shown in FIG. 8b) to move outward, see for example 88e' in FIG. 8b, releasing said snaps from locking ridge 89d and allowing the removal of venous reservoir 772.

Chamber 87, formed between venous reservoir 772 and rigid housing 88, communicates via port 88c with vacuum regulator 813, said regulator used to adjust the degree of suction applied to chamber 87 using knob 813b. Gauge 813a can be used to indicate the applied suction. As described before, venous reservoir 772 responds to pressure differences across its walls 18 and 19 (FIG. 8b). Thus, diminished blood flow from patient 1102, see FIG. 1, due to increased resistance to flow (e.g. smaller cannula) can be increased by applying suction to chamber 87. The suction "pulls" walls 18 and 19 outward thereby pulling the blood into the blood chamber. For safety, housing 88 is sized to assure that venous reservoir 772 cannot over-expand. Thus, as chamber 8 of venous reservoir 772 expands, walls 18 and 19 move towards the walls of housing 88 until they make contact, see 18a and 19a in FIG. 8b. Once contact is made, further outward motion of walls 18 and 19 is limited by rigid housing 88. To facilitate the use of the system, housing 88 incorporates pole clamp 810, said clamp provides a simple connection of said housing to a heart-lung machine. It should be understood that a rigid component, such as rigid cylinder 72, incorporating into venous reservoir 772, see FIGS. 7a and 8a, is required to facilitate both the introduction of said venous reservoir 772 into housing 88, and the sealing of said reservoir against gasket 81, shown in FIG. 8a. To enhance the ability of the user to see the blood in venous reservoir 772, light 80, shown in FIG. 8b, can be added to the back of housing 88.

FIG. 9a illustrates another embodiment for a nondisposable housing designed to allow venous augmentation with a collapsible venous reservoir. The concept is similar to that shown in FIG. 8a except that the seals and closure mechanism are different. Here, venous reservoir 772 is placed in container 98, said container having a back plate and four walls forming first open box, 98e, which accommodates venous reservoir 772. Container 98 has a matching door 99 that is hinged at 99f by pin 98f to container 98 and is shown in FIGS. 9b and 9c. Door 99 has a front plate and four walls forming second box 99e that also accommodates venous reservoir 772. To operate, venous reservoir 772 is placed in first box 98e and door 99 is closed thereby sealing said venous reservoir, along gasket 92, within the sealed space formed by first box 98e and second box 99e. Port 98c in box 98 is in fluid communication with said formed sealed space, and preferably is connected to a regulated vacuum source, much like the one described in reference to port 88c shown in FIGS. 8a and 8b. It should be understood that for proper function, the venous reservoir is free to expand within the sealed space thus formed. For free expansion of venous reservoir 772, seals of the venous reservoir within container 98 and door 99 are achieved at inlet tube 1, between 92a and 99a (FIG. 9b), air-venting tube 4, at 92b and 99b (FIG. 9c), and along outlet tube 5, at 92c and 99c (FIG. 9b). When door 99 is closed, the ID of indentations 92a and 99a form a tight seal about the OD of inlet tube 1. Similarly, indentations 92c and 99c form a tight seal about the outside of outlet tube 5 (FIG. 9b), and indentations 92b and 99b form a tight seal about the outside of air-venting tube 4 (FIG. 9c). To assure a tight seal, relievable latches 99d lock unto ridge 98d, see FIGS. 9a, 9b and 9c.

To improve the seal along the inlet, outlet and gas exhaust port, each of said tubes preferably incorporates a secondary structure, see sealing structure 1a in FIG. 9d for inlet tube 1. Sealing structure 1a has a flexible wall forming wings 1aa and 1ab on the side of tube 1, see FIGS. 9e and 9d. The wings are tapered, being thickest at the base and thinnest at the tips, see FIG. 9d. For effective sealing, gasket 92 accommodates wing 1aa at thinner section 92aa and wing 1ab at thinner section 92ab, said accommodation providing a seal between container 98 and door 99 along gasket 92. Gasket 92, for example, can be made of a polyurethane sponge, which conform to the shape of said wings, see FIG. 9d. Wing 1a preferably is bonded or welded to tube 1 and is therefore disposed when venous reservoir 772 is disposed. In one preferred embodiment, shown in FIGS. 9b, 9c and 9d, indentation 98a in the housing 98 and indentation 99a in door 99 approximate half the outside diameter of inlet tube 1. Similar embodiment can be incorporated to seal airventing tube 4 and outlet tube 5.

FIG. 9f illustrates another preferred embodiment for sealing inlet tube 1 between housing 98 and door 99. Here, gasket 93 is attached to door 99, said gasket having indentation 93a to seal about inlet tube 1 when door 99 is closed against housing 98. This design also incorporates deeper indentation 98a′ in the housing, with a closed circumference greater than 225° and an inside diameter that is less than the OD of inlet tube 1. When the venous reservoir is loaded into the housing, flexible inlet tube 1 is pushed into indention 98a′ where it is retained within said indentation by a pressure fit. This allows the user to load air-venting tube 4 and outlet tube 5. It to should be obvious that purge port should be loaded first thereby having the venous reservoir hanging from the top while the other two tubes are lined up before door 99 is closed.

The scope of the invention should not be limited to the aforementioned embodiments. The invention can be extended to other embodiments as illustrated with the venous reservoir having a single flexible wall assigned to Cordis Dow Corp and made by C. R. Bard (U.S. Pat. No. 4,424,190). Currently, there are no means to apply suction to the venous blood utilizing this Bard venous reservoir. With the present invention, applying suction to this design of a venous reservoir is simple. FIGS. 10a, a three dimensional view, 10b, a cross sectional view of 103, and 10c, a cross sectional view along lines 10c and 10c′ shown in FIG. 10b, all illustrate a modification of the venous reservoir component shown in FIG. 1 of U.S. Pat. No. '190. Blood enters venous reservoir 103 at inlet 101 into chamber 102, said chamber formed by rigid wall 1019 and flexible wall 1018, shown in a semi-full position. Wall 1018 is also shown in an almost empty position as indicated by dashed line 1018′. Flexible wall is sealed to rigid wall 1019 along periphery 1019a, said seal made by solvent bonding, RF welding, ultrasonic welding or other appropriate method. Air entering expandable blood chamber 102 is extracted via gas exhaust port 104. Gas exhaust port 104 may incorporate an automated gas removal means, as shown for example, utilizing a hydrophobic membrane as described in reference to FIG. 5a. Blood exits via outlet tube 105. For augmented venous return, the present invention adds face plate 108 that seals the external surface of flexible wall 1018 along periphery 108a of face plate 108, forming sealed pressure chamber 107. The seal 108a and seal 1019a therefore can sandwich the free ends of flexible wall 1018 and can be made simultaneously. Gas port 108b is in fluid communication with sealed pressure chamber 107, and is preferably connected to vacuum regulator 813 shown and previously described in reference to FIG. 8a. Faceplate 108, is preferably clear and rigid such as clear PVC, polycarbonate, polyester, or alike. Faceplate 108 does not have to be biocompatible because it does not contact blood. It should be clear that by incorporating sealing means between faceplate 108 and flexible wall 1018, similar to those described in reference to FIG. 8a, faceplate 108 could be made nondisposable. Whether disposable or not, faceplate 108 forming pressure chamber 107 allows the user to apply suction to chamber 107 via port 108b, said suction transmitted to the blood via flexible wall 1018 thereby providing augmented venous return.

FIG. 10b shows nondisposable cover 108 held against disposable rigid structure 1019. When vacuum is applied to suction port 108b of nondisposable cover 108, the user would hold cover 108 against periphery 1019a of structure 1019. The suction within chamber 107 pulls disposable structure 1019 and nondisposable cover 108 together. Thus, the pressure difference across cover 108 is used for forming a tighter seat and holding cover 108. Should vacuum fail, any pressure buildup in chamber 107 would push faceplate 108 open to relieve said pressure.

It should be understood that a comprehensive description of each of the applications of the invention is beyond the scope of a patent application and therefore the aforementioned descriptions are given as illustrations and should not be used to limit the intent, spirit, or scope of the invention.

With that in mind, I claim:

1. The combination of a disposable blood reservoir and a rigid housing for vacuum assisted venous drainage, in a sterile extracotporeal circuit, said combination comprising:
    a) said disposable blood reservoir having a first wall and a second wall, said first wall having a first periphery, said first wall having an inner blood side and an external side, said second wall having a second periphery, an inner blood side and an external side, said first wall being a flexible wall, said first wall sealed along its first periphery to said second wall along said second periphery thereby forming a blood chamber having at least one flexible wall, said blood chamber adapted to contain a physiological liquid at a first pressure,
    b) said disposable blood reservoir having an inlet tube, an outlet tube, and a gas purge tube to provide fluid communication between said blood chamber and said extracorporeal circuit,
    c) at least a first and a second rigid structure that when combined form said rigid housing,
    d) at least one of said rigid structures being disposable and integrated with said disposable blood reservoir,
    e) a gas port formed in one of said rigid structure, said port adapted to be in fluid communication with a vacuum source,
    f) at least one of said inlet, outlet or purge tubes passing through and is sealed within said disposable rigid structure, wherein said rigid structures are combined to form said rigid housing that seals said flexible wall of said blood chamber within said rigid housing, with said gas port providing a second pressure within said rigid housing when said housing is sealed, said second pressure being transmitted across said at least one flexible wall to affect the first pressure of said physiological liquid in said blood chamber, said combination formed by an end user without compromising the sterility of said extracorporeal circuit.

2. The combination of a blood reservoir, and a rigid housing, as claimed in claim 1, wherein the second wall is flexible, with said first and second flexible walls of said blood chamber sealed within said rigid housing.

3. The combination of a blood reservoir and a rigid housing, as claimed in claim 1 wherein said inlet and said outlet tubes pass through and are sealed within said disposable rigid structure.

4. The combination of a disposable blood reservoir and a rigid housing for vacuum assisted venous drainage, in a sterile extracorporeal circuit, said combination comprising:

a) said disposable blood reservoir having a first wall and a second wall said first wall having a first periphery, said first wall having an inner blood side and an external side, said second wall having a second periphery, an inner blood side and an external side, said first wall being a flexible wall, said first wall sealed along its first periphery to said second wall along said second periphery thereby forming a blood chamber having at least one flexible wall, said blood chamber adapted to contain a physiological liquid at a first pressure, b) said disposable blood reservoir having an inlet tube, an outlet tube, and a gas purge tube to provide fluid communication between said blood chamber and said extracorporeal circuit, c) at least a first and a second rigid structure that when combined form said rigid housing, said first and second rigid structures being nondisposable, d) a gas port formed in one of said first or said second rigid structures, said port adapted to be in fluid communication with a vacuum source, wherein said rigid structures form a clamshell like rigid housing that seals said flexible wall of said blood chamber within said rigid housing, with said gas port providing a second pressure within said rigid housing when said housing is sealed, said second pressure being transmitted across said at least one flexible wall to affect the first pressure of said physiological liquid in said blood chamber, said combination formed by an end user without compromising the sterility of said extracorporeal circuit.

5. The combination of a blood reservoir and a rigid housing, as claimed in claim 4 wherein said nondisposable rigid structures form a clamshell like rigid housing and are connected to each other with a hinge along a common side.

6. The combination of a disposable blood reservoir and a rigid housing for vacuum assisted venous drainage, in a sterile extracorporeal circuit, said combination comprising:

a) said disposable blood reservoir having a first flexible wall and a second rigid wall said first wall having a first periphery, said first wall having an inner blood side and an external side, said second wall having a second periphery, an inner blood side and an external side, said first wall sealed along its first periphery to said second wall along said second periphery thereby forming a blood chamber having at least one flexible wall, said blood chamber adapted to contain a physiological liquid at a first pressure, b) said disposable blood reservoir having an inlet tube, an outlet tube, and a gas purge tube to provide fluid communication between said blood chamber and said extracorporeal circuit, c) at least a first rigid structure that when combined with said second rigid wall form said rigid housing, d) a gas port formed in said second rigid structures, said port adapted to be in fluid communication with a vacuum source, wherein said first rigid structure and said second rigid wall are combined to form said rigid housing that seals said flexible wall of said blood chamber within said rigid housing, with said gas port providing a second pressure within said rigid housing when said housing is sealed, said second pressure being transmitted across said at least one flexible wall to affect the first pressure of said physiological liquid in said blood chamber, said combination formed by an end user without compromising the sterility of said extracorporeal circuit.

7. The combination of a blood reservoir and a rigid housing, as claimed in claim 6, wherein said inlet tube, said outlet tube, and said gas purge tube are connected respectively to an inlet port, an outlet port and a gas purge port formed in said second rigid wall, said ports providing fluid communication between said blood chamber and said extracorporeal circuit.

* * * * *